United States Patent
Pierson et al.

(10) Patent No.: US 6,612,465 B2
(45) Date of Patent: Sep. 2, 2003

(54) MULTI-COMPONENT MIXING STORAGE AND DISPENSING DEVICE

(75) Inventors: Paul R. Pierson, Camden, DE (US); Paul D. Hammesfahr, Wyoming, DE (US)

(73) Assignee: Dentsply Research & Development Corp.

( * ) Notice: Subject to any disclaimer, the term of this patent is extended or adjusted under 35 U.S.C. 154(b) by 0 days.

(21) Appl. No.: 10/121,000

(22) Filed: Apr. 11, 2002

(65) Prior Publication Data

US 2002/0160333 A1 Oct. 31, 2002

Related U.S. Application Data

(63) Continuation of application No. 09/975,486, filed on Oct. 11, 2001.
(60) Provisional application No. 60/240,720, filed on Oct. 16, 2000, and provisional application No. 60/240,459, filed on Oct. 13, 2000.

(51) Int. Cl.[7] .............................. A61C 5/04; B67D 5/52
(52) U.S. Cl. ..................... 222/82; 222/86; 222/137; 222/145.5; 222/145.6; 433/90; 604/191
(58) Field of Search ...................... 433/90; 604/191; 222/137, 145.1, 145.5, 145.6, 82, 86

(56) References Cited

U.S. PATENT DOCUMENTS

| | | | |
|---|---|---|---|
| 2,826,339 A | 3/1958 | Maillard | 222/137 |
| 3,166,221 A | 1/1965 | Nielsen | 222/137 |
| 3,262,608 A | 7/1966 | Macey | 222/386 |
| 3,330,444 A | 7/1967 | Raypholtz | 222/137 |
| 3,595,439 A | 7/1971 | Newby | 222/80 |
| 3,767,085 A * | 10/1973 | Cannon et al. | 222/137 |
| 4,215,985 A | 8/1980 | Madlener | 433/90 |
| 4,515,267 A | 5/1985 | Welsh | 206/219 |
| 4,648,532 A | 3/1987 | Green | 222/82 |
| 4,708,650 A | 11/1987 | Holewinski et al. | 433/90 |
| 4,767,026 A | 8/1988 | Keller et al. | 222/137 |
| 4,767,326 A | 8/1988 | Bennett et al. | 433/90 |
| 4,776,704 A | 10/1988 | Kopunek et al. | 366/184 |
| 4,869,400 A | 9/1989 | Jacobs | 222/137 |
| 4,950,237 A | 8/1990 | Henault et al. | 604/82 |
| 4,952,068 A | 8/1990 | Flint | 366/337 |
| 4,972,969 A | 11/1990 | Randklev | 222/1 |
| 4,995,540 A | 2/1991 | Colin et al. | 222/132 |
| 4,997,371 A | 3/1991 | Fischer | 433/90 |
| 5,004,124 A | 4/1991 | Stefaniak et al. | 222/136 |
| 5,033,650 A | 7/1991 | Colin et al. | 222/137 |
| RE33,801 E | 1/1992 | Green | 222/82 |
| 5,137,178 A | 8/1992 | Stokes et al. | 222/94 |

(List continued on next page.)

FOREIGN PATENT DOCUMENTS

| | | |
|---|---|---|
| AU | 667 375 | 3/1996 |
| CA | 2101137 | 4/1996 |
| DE | 93 03 268 | 7/1994 |
| DE | 196 28 552 | 2/1997 |
| DE | 19648820 | 5/1998 |
| DE | 69322612D | 1/1999 |
| DE | 69322612 T | 7/1999 |
| EP | 0 237 182 | 9/1987 |
| EP | 319 639 | 6/1989 |
| EP | 608 598 | 12/1998 |
| EP | 0 919 206 | 6/1999 |
| ES | 2127791 T | 5/1999 |
| WO | 91 05731 | 5/1991 |

*Primary Examiner*—Kenneth Bomberg
(74) *Attorney, Agent, or Firm*—Douglas J. Hura; James B. Bieber

(57) ABSTRACT

A multi-component, mixing, storage and dispensing package (10) has a housing 11, a displaceable cavity block (20) having at least one cavity (21) therein. A vent spike block (40) having at least one spike (42) held in an opposing relation to at least one cavity (21) is provided within the housing (11). When cavity block (21) is caused to move toward the vent spike block (40) spike (42) is caused to enter a cavity (21). A vent (43) is in fluid communication through the spike (42) with a mix channel (51) and a mixing and dispensing tip (50).

1 Claim, 2 Drawing Sheets

U.S. PATENT DOCUMENTS

| | | | |
|---|---|---|---|
| 5,172,807 A | 12/1992 | Dragan et al. | 206/219 |
| 5,195,663 A | 3/1993 | Martin et al. | 222/327 |
| 5,242,082 A * | 9/1993 | Giannuzzi | 222/137 |
| 5,246,371 A | 9/1993 | Fischer | 433/217.1 |
| 5,267,859 A | 12/1993 | Discko, Jr. | 433/89 |
| 5,269,684 A | 12/1993 | Fischer | 433/90 |
| 5,273,190 A | 12/1993 | Lund | 222/83 |
| 5,286,257 A | 2/1994 | Fischer | 604/82 |
| 5,314,412 A * | 5/1994 | Rex | 604/191 |
| 5,333,760 A | 8/1994 | Simmen | 222/137 |
| 5,336,088 A | 8/1994 | Discko, Jr. | 433/90 |
| 5,348,392 A * | 9/1994 | Bouquet et al. | 222/137 |
| 5,401,169 A | 3/1995 | Fleisher et al. | 433/90 |
| 5,443,182 A | 8/1995 | Tanaka et al. | 222/137 |
| 5,501,371 A | 3/1996 | Schwartz-Feldman | 222/136 |
| 5,554,665 A | 9/1996 | Tateosian et al. | 522/30 |
| 5,584,815 A | 12/1996 | Pawelka | 604/191 |
| 5,609,271 A | 3/1997 | Keller et al. | 222/145.6 |
| 5,624,260 A | 4/1997 | Wilcox et al. | 433/90 |
| 5,697,524 A | 12/1997 | Sedlmeier | 222/82 |
| 5,707,234 A | 1/1998 | Bender | 433/90 |
| 5,710,194 A | 1/1998 | Hammesfahr et al. | 523/116 |
| 5,722,829 A | 3/1998 | Wilcox et al. | 433/90 |
| 5,743,436 A | 4/1998 | Wilcox et al. | 222/137 |
| 5,788,122 A | 8/1998 | Keller | 222/137 |
| 5,816,804 A | 10/1998 | Fischer | 433/90 |
| 5,829,976 A | 11/1998 | Green | 433/89 |
| 5,848,894 A | 12/1998 | Rogers | 433/90 |
| 5,871,355 A | 2/1999 | Dragan et al. | 433/90 |
| 5,875,791 A | 3/1999 | Sheffler et al. | 132/218 |
| RE36,235 E | 6/1999 | Keller et al. | 222/137 |
| 5,924,600 A | 7/1999 | Keller | 222/137 |
| 6,048,201 A | 4/2000 | Zwingenberger | 433/90 |
| 6,059,570 A | 5/2000 | Dragan et al. | 433/80 |
| 6,065,645 A | 5/2000 | Sawhney et al. | 222/137 |
| 6,079,871 A | 6/2000 | Jonas et al. | 366/336 |
| 6,083,002 A | 7/2000 | Martin et al. | 433/90 |
| 6,092,649 A | 7/2000 | Sergio et al. | 206/222 |
| 6,095,813 A | 8/2000 | Broyles | 433/80 |
| 6,095,814 A | 8/2000 | Petrich et al. | 433/90 |
| 6,099,307 A | 8/2000 | Discko, Jr. | 433/90 |
| 6,129,243 A | 10/2000 | Pal et al. | 222/94 |
| 6,129,244 A | 10/2000 | Horth | 222/94 |
| 6,135,771 A | 10/2000 | Dragan et al. | 433/90 |
| 6,213,633 B1 | 4/2001 | Kramer et al. | 366/339 |
| 6,569,113 B2 * | 5/2003 | Wirt et al. | 604/191 |

* cited by examiner

MULTI-COMPONENT MIXING STORAGE AND DISPENSING DEVICE

This application is a continuation of application Ser. No. 09/975,468, filed Oct. 11, 2001; pending, which claims benefit of Provisional No. 60/240,459, filed Oct. 13, 2000, and claims benefit of Provisional No. 60/240,720, filed Oct. 16, 2000.

TECHNICAL FIELD

The present invention is directed toward a package for holding at least two materials. More particularly, the invention is directed toward a package for holding the materials and dispensing them when needed. Specifically, the invention is directed toward a package for holding at least two materials which can be mixed at the time of dispensing.

BACKGROUND OF THE INVENTION

In certain arts, such as in the dental industry, it is often required to mix two materials prior to use. For example, it is sometimes necessary to mix a monomer with an initiator to prepare a polymeric adhesive, or the like. Especially in the dental industry, it is also desirable to provide only enough material for a given application because application of such materials in the oral cavity often include small amounts. It has been common practice to package a multitude of dental materials, dual component or not, as a single use or unit dose package.

With the unit doses employed in the dental industry, it is sometimes difficult to dispense the multiple components required to form a material, and mix them prior to use. Again, the small amounts employed make such mixing difficult. Further, it has been the practice that larger quantities of the individual components are stored separately and then mixed prior to use.

A need exists therefore, for a multi-component package, which not only separates the components during storage, but which also facilitates the mixing and dispensing of those materials.

SUMMARY OF THE INVENTION

A multi-component, mixing, storage and dispensing package, preferably a unit dose package, includes a housing having a mixing tip attached at one end thereof. The mixing tip has an outlet orifice and an input orifice fluidly connected by a mixing channel. The inlet orifice is in fluid communication with a housing mix channel which in turn is in fluid communication with a vent spike block. The vent spike block includes at least one spike having a vent or open channel therethrough. The housing further includes a displaceable cavity block having at least one cavity therein, and displaceable in a direction toward said vent spike block. In this manner, when the vent within the vent spike is caused to enter the cavity, material contained within the cavity is caused to travel through the vent toward the mix channel in the housing. From the mix channel in the housing, the material is then caused to travel through the mix channel in the dispensing end and out of the dispensing orifice outlet. More preferably, the vent spike block includes at least two spikes corresponding to at least two cavities in the cavity block. Further, each vent in the vent spikes is caused to fluidly communicate with the secondary mix channel in the housing. Mixing of the materials from the two cavities is thereby effected in the secondary mix channel and the mix channel of the dispensing tip.

PREFERRED EMBODIMENTS FOR CARRYING OUT THE INVENTION

Figure 1:
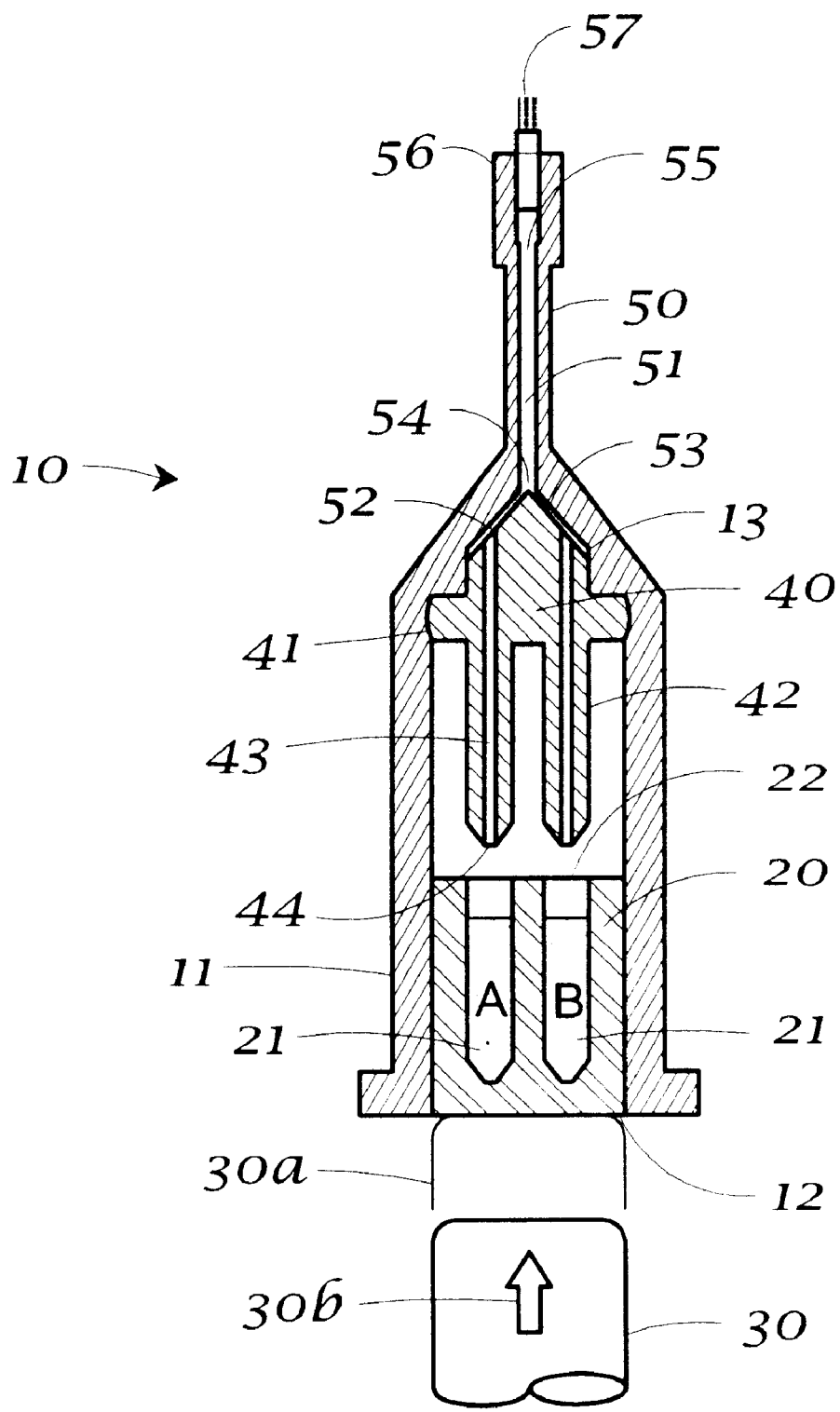
FIG. 1 is a front elevational, sectional view of a storage and dispensing package according to the present invention.

A multi-component, mixing, storage and dispensing package is shown by way of example on the drawings by the number 10. Although package 10 can be used for the dispensing of any material, in a preferred embodiment, the package 10 is particularly adapted for the storage, mixing and dispensing of dental materials. Further, package 10, while it can be of any size and therefore, useful for the storage and dispensing of any amount of materials, it is also, in a preferred embodiment, adapted for a unit dose of dental material.

Package 10 includes a housing 11 having an input end 12 and an output end 13. Contained within housing 11 is a cavity block 20. Preferably, the interior of housing 11 is cylindrical, and housing block 20 is configured to the approximate same size of the hollow interior of housing 11. Further, cavity block 20 is preferably axially displaceable or slidable within housing 11, in an approximate or substantially axial manner.

Cavity block 20 preferably includes at least one, and more preferably, a plurality of cavities 21. Cavities 21 may be the same size, different sizes or any other configuration. It is preferred that cavities 21 be configured to hold a unit dose of materials to be mixed, dispensed and used for a single application of such material. A seal, such as a foil seal 22 encloses cavities 21, such that the materials therein are held in place, and cannot mix, until desired. As will be more fully explored below, foil seal 22 is ruptured or otherwise removed when it is desired to mix and dispense the materials in cavities 21.

A means of moving cavity block 20 within housing 11 is required. One such means is a plunger 30 of any configuration. Plunger 30 may be a standard syringe plunger, the syringe itself not being shown in the drawings, or any other sort of plunger activating device. For example, DENTSPLY International Inc. manufactures a device known as a Compule® Gun, for use in dispensing among other things, the TPH Spectrum composite. Any such plunger activating device is useful in the present invention. Shown on the drawings is only a plunger 30, with the understanding that plunger 30 can be manually, mechanically, or otherwise activated in a conventional manner.

As shown by phantom line 30A on the drawings, plunger 30 can be moved into a position as shown by arrow 30B such that it is in physical contact with cavity block 20, thereby moving cavity block 20 within housing 11. At an end distal from input end 12 of housing 11, there is provided a vent spike block 40. Vent spike block 40 is held in a preferably static position within housing 11, such by use of positioning tabs 41 physically engaging interior of housing 11. Vent spike block 40 is provided with at least one and more preferably a plurality of spikes 42. When spike block 40 is held within housing 11, spikes 42 are positioned in a generally opposing relation to cavities 21. It is further preferred that the exterior of spikes 42 at least somewhat and more preferably substantially conform to the dimensions and shape of cavities 21, although this is not necessarily required for the practice of the present invention. Each spike 42 is further provided with a vent 43 substantially therethrough. More preferably, each spike 42 has a longitudinal dimension, and each vent 43 is substantially parallel to this longitudinal dimension. More preferred still, each vent 43 is positioned in the substantial axial center of each spike 42, although this is not necessarily required.

As will be appreciated, as plunger 30 is caused to physically contact cavity block 20, cavity block 20 will be caused to move in a direction toward spikes 42. Spikes 42 will be caused to enter cavities 21, with sufficient displacement of cavity block 20. If used, foil seal 22 is punctured or otherwise displaced by physical interaction with spikes 42. To facilitate the puncturing of foil seal 22, spikes 42 may be provided with a sharp end 44, as depicted in the drawings.

It will also be appreciated that as spikes 42 enter cavities 21, the material within each cavity 21 will be displaced. Because spike 42 is preferably configured to be similarly dimensions to cavity 21, the only place for the material to go within cavity 21 is to be displaced through vent 43.

Vent 43 through each spike 42 preferably fluidly communicates with a dispensing or mix tip 50. Mix tip 50 is preferably elongated having a mix channel 51 therein. Mix channel 51 preferably communicates with each vent 43, such as through a secondary mix channel 52. Ribs 53 may be provided between vent spike block 40 and mix tip 50 to allow fluid communication between vents 42 and mix channel 51. Mix tip 50 therefore, preferably has an input orifice 54 and an outlet orifice 55. Mix tip 50 may also be provided with a brush tip 56 containing brushes 57.

Mix tip 50 is preferably configured from a bendable plastic material, such that tip 50 may be bent into any desired position to facilitate the placement of the material being dispensed. Further, although not shown in the drawings, the mix tip 50 may also contain a mix element.

It will again be appreciated that as cavity block 20 is caused to move in a direction toward vent spike block 40, spikes 42 will enter respective opposing cavities 21, thereby causing the material within cavities 21 to be displaced through vents 43, and because vents 43 are in fluid communication with mix channel 51, each of the materials from cavities 21 will be caused to enter mix channel 51, thereby mixing. This mixed material can then be dispensed through outlet orifice 55. If employed, brushes 57 will be coated or will otherwise contact the material flowing through outlet orifice 55. Brushes 57 can then be used to apply the material wherever desired.

Figure 2:
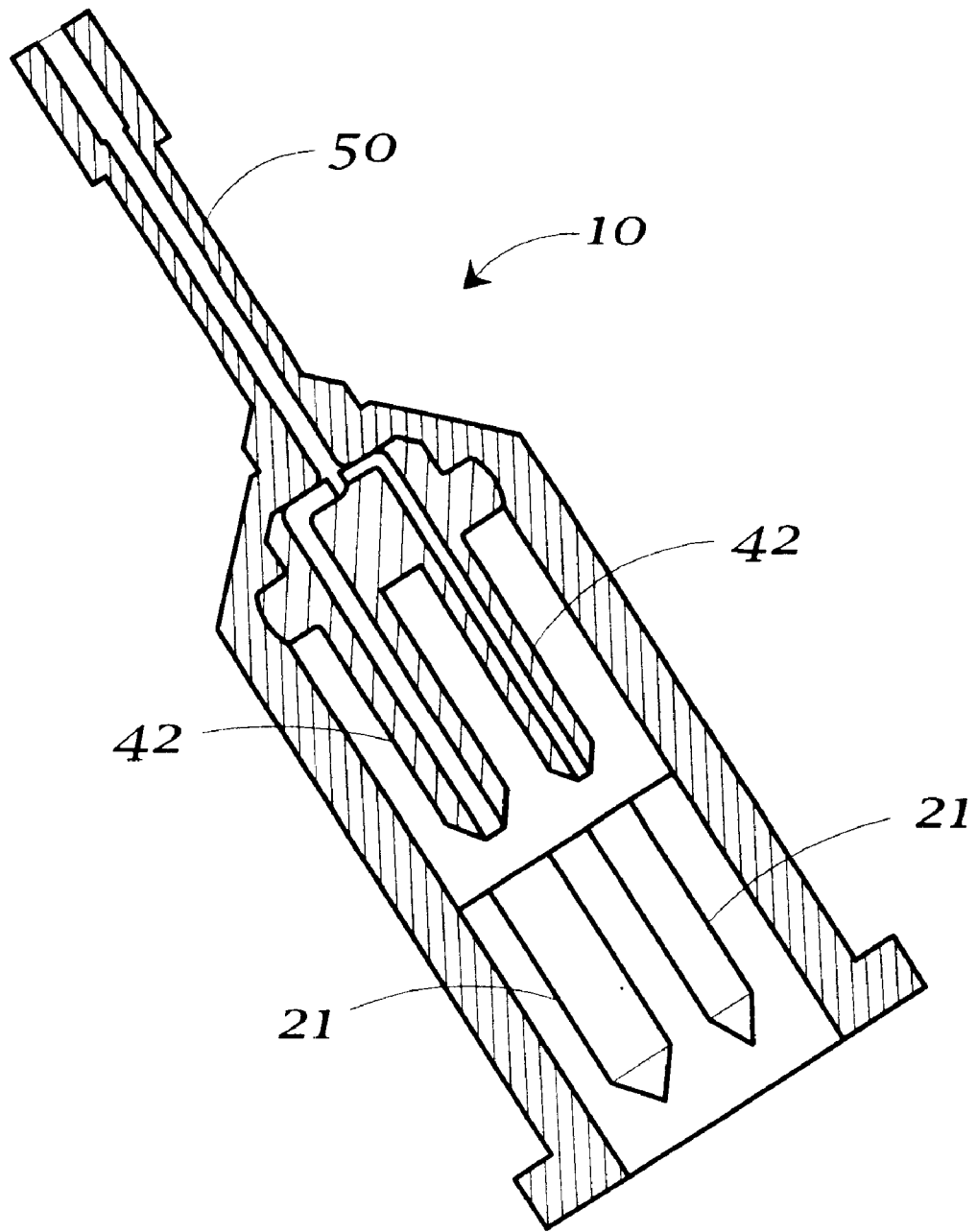
FIG. 2 is a sectional, perspective view of another embodiment of the storage and dispensing package of FIG. 1.

As will also be appreciated, cavities 21 can be of any size as may be required for a particular application. Also, any number of cavities 21 may be employed as required, and may also be of any size. It is sometimes the case of the materials to be mixed that more of one material is required as opposed to another. As shown in FIG. 2, spikes 42 of different sizes, corresponding to cavities 21 of different sizes are employed.

It is also preferred that cavities 21 be configured to hold the precise amount of material desired. For example, cavities 21 may be configured such that a unit dose of material is stored.

It should be evident therefore, that a storage and dispensing package as described accomplishes the objects of the present invention. An exemplary such package has been described and shown on the drawings, without attempting to show all of the variations that fall within the scope of the invention.

We claim:

1. A multi-component, mixing, storage and dispensing package comprising:

a housing having a mixing tip attached at one end thereof, said mixing tip having an outlet orifice and an input orifice fluidly connected by a mixing channel; said inlet orifice being in fluid communication with a housing mix channel which in turn is in fluid communication with a vent spike block; said vent spike block having at least two spikes, each said spike having a vent therethrough; said housing further including a displaceable cavity block having at least two cavities therein, each said cavity containing a dental material; said cavity block being displaceable in a direction toward said vent spike block; each of said spikes being in a parallel and opposed relation to one of said cavities; such that when each said spike is caused to enter one of said cavities, material contained within said cavity is caused to travel through the respective said vent toward said mix channel in said housing; and, such that continued displacement of said cavity block toward said spike block causes material from each said cavity to travel through said mix channel thereby causing physical, mixing contact between the dental materials from each said cavity, and the discharge of the mixed dental materials from said outlet orifice.

\* \* \* \* \*